United States Patent
Prencipe et al.

(10) Patent No.: US 10,576,032 B2
(45) Date of Patent: *Mar. 3, 2020

(54) ORAL CARE COMPOSITION COMPRISING SERINE AND AT LEAST A ZINC SALT

(71) Applicant: Colgate-Palmolive Company, New York, NY (US)

(72) Inventors: Michael Prencipe, Princeton Junction, NJ (US); Yun Xu, Guangzhou (CN); Xiao Yi Huang, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/104,780

(22) PCT Filed: Dec. 10, 2014

(86) PCT No.: PCT/US2014/069445
§ 371 (c)(1),
(2) Date: Jun. 15, 2016

(87) PCT Pub. No.: WO2015/094836
PCT Pub. Date: Jun. 25, 2015

(65) Prior Publication Data
US 2016/0317409 A1     Nov. 3, 2016

(30) Foreign Application Priority Data

Dec. 19, 2013   (CN) .......................... 2013 1 0702992

(51) Int. Cl.
| | | |
|---|---|---|
| *A61K 8/44* | (2006.01) | |
| *A61K 8/27* | (2006.01) | |
| *A61Q 11/00* | (2006.01) | |
| *A61K 8/365* | (2006.01) | |

(52) U.S. Cl.
CPC .................. *A61K 8/44* (2013.01); *A61K 8/27* (2013.01); *A61K 8/365* (2013.01); *A61Q 11/00* (2013.01)

(58) Field of Classification Search
CPC . A61K 8/27; A61K 8/365; A61K 8/44; A61Q 11/00
See application file for complete search history.

(56) References Cited

U.S. PATENT DOCUMENTS

| | | | |
|---|---|---|---|
| 8,153,126 | B2 | 4/2012 | Leone |
| 9,408,794 | B2 | 8/2016 | Lewus |
| 9,579,269 | B2 | 2/2017 | Mello |
| 2008/0181856 | A1 | 7/2008 | Prencipe |
| 2010/0256369 | A1 | 10/2010 | Suga et al. |
| 2012/0201762 | A1 | 8/2012 | Pilch et al. |
| 2013/0017240 | A1 | 1/2013 | Porter et al. |
| 2017/0128340 | A1 | 5/2017 | Mello |

FOREIGN PATENT DOCUMENTS

| | | |
|---|---|---|
| EP | 2055777 | 5/2009 |
| WO | WO 00/06108 | 2/2000 |
| WO | WO 2006/012987 | 2/2006 |
| WO | WO 2008/006725 | 1/2008 |
| WO | WO 2011/053273 | 5/2011 |
| WO | WO 2011/123123 | 10/2011 |
| WO | WO 2012/087288 | * 6/2012 |
| WO | 2016/058140 | 4/2016 |

OTHER PUBLICATIONS

International Search Report and Written Opinion mailed in International Application No. PCT/US2014/069445 dated Apr. 15, 2015.
Sobel, S. et al. "The complexation of aqueous metal ions relevant to biological applications. 1. Poorly soluble zinc salts and enhanced solubility with added amino acid" *Chemical Speciation and Bioavailability* 2008; 20(2); 93-98.
Sobel, S. et al. "The complexation of aqueous metal ions relevant to biological applications. 2. Evaluation of simultaneous equilibria of poorly soluble zinc salts with select amino acids" *Chemical Speciation and Bioavailability* 2010: 22(3); 201-205.

* cited by examiner

*Primary Examiner* — Lezah Roberts

(57) ABSTRACT

An oral care composition comprising serine and one or more zinc salts for use in reducing or inhibiting biofilm formation in an oral cavity.

12 Claims, No Drawings

ORAL CARE COMPOSITION COMPRISING SERINE AND AT LEAST A ZINC SALT

BACKGROUND

Dental plaque is a biofilm that adheres to tooth and other oral surfaces, particularly at the gingival margin, and is implicated in the occurrence of gingivitis, periodontitis, caries and other forms of periodontal disease. Dental plaque is cohesive and highly resistant to removal from teeth and/or oral surfaces. Dental plaque comprises glucans, which are insoluble polysaccharides that provide plaque with its cohesive properties. The bacterial enzyme glucosyltransferase converts dietary sugar into glucans. Plaque mineralizes to form a hard deposit called calculus (or tartar), which becomes a local irritant for the gums, causing gingivitis.

Various antibacterial agents can retard the growth of bacteria and thus reduce the formation of biofilm on oral surfaces.

Zinc and other metal compound/salts have been previously used as antibacterial agents. Without being bound by any theory, free zinc ions are believed to provide antibacterial efficacy by inhibition of glucose metabolism and/or interaction with the bacterial cell wall, reducing bacterial colonization of the oral cavity (as discussed in Cummins D., *J Clin Periodontol* 1991; 18; 455-461). An insoluble zinc compound, zinc oxide, could also deliver strong antibacterial efficacy during tooth brushing.

It would be desirable to provide an oral care composition which exhibits even greater biofilm reduction efficacy than previously-known compositions.

BRIEF SUMMARY

Provided is an oral care composition comprising: (a) serine; and (b) zinc oxide and zinc citrate in a weight ratio of zinc oxide to zinc citrate of 1.5:1 to 4.5:1.

Optionally, the composition has a weight ratio of zinc oxide to zinc citrate of 1.5:1 to 4:1, 1.7:1 to 2.3:1, 1.9:1 to 2.1:11, or about 2:1. Also, the corresponding molar ratios based on these weight ratios can be used.

Optionally, the composition comprises serine in an amount of 0.05 weight % to 0.8 weight %, or 0.075 weight % to 0.25 weight %, based on the total weight of the composition. Further optionally, the composition comprises serine in an amount of from 0.12 weight % to 0.25 weight %, based on the total weight of the composition. Further optionally, the composition comprises serine in an amount of from 0.14 weight % to 0.20 weight %, based on the total weight of the composition. Still further optionally, the composition comprises serine in an amount of about 0.15 weight %, based on the total weight of the composition.

Optionally, the composition comprises zinc oxide in an amount of from 0.5 weight % to 1.5 weight % and zinc citrate in an amount of from 0.25 weight % to 0.75 weight %, based on the total weight of the composition, Further optionally, the composition comprises zinc oxide in an amount of about 1 weight % and zinc citrate in an amount of about 0.5 weight %, based on the total weight of the composition.

Also provided is an oral care composition comprising: (a) serine and one or more zinc salts; for use in reducing or inhibiting biofilm formation in an oral cavity.

Optionally, serine is present in the composition in an amount of from 0.05 weight % to 0.8 weight %, based on the total weight of the composition. Further optionally, serine is present in the composition in an amount of 0.05 weight % to 0,39 weight %, based on the total weight of the composition. Still further optionally, the composition comprises serine in an amount of from 0.075 weight % to 0.25 weight %, based on the total weight of the composition. Still further optionally, the composition comprises serine in an amount of from 0.12 weight % to 0.25 weight %, based on the total weight of the composition. Further optionally, the composition comprises serine in an amount of from 0.14 weight % to 0.20 weight %, based on the total weight of the composition. Still further optionally, the composition comprises serine in an amount of about 0.15 weight %, based on the total weight of the composition.

Optionally, the molar ratio of serine:total zinc salts is from 0.01:1 to 3:1.

Optionally, the total concentration of zinc salts in the composition is from 0.2 weight % to 5 weight %, based on the total weight of the composition.

Optionally, at least one of said one or more zinc salts is zinc oxide.

Optionally, at least one of said one or more zinc salts is zinc citrate.

Optionally, the composition comprises zinc oxide in an amount of from 0.5 weight % to 1.5 weight % and zinc citrate in an amount of from 0.25 weight % to 0.75 weight %, based on the total weight of the composition. Further optionally, the composition comprises zinc oxide in an amount of about 1 weight % and zinc citrate in an amount of about 0.5 weight %, based on the total weight of the composition.

Also provided is a method of reducing or inhibiting biofilm formation in an oral cavity, the method comprising contacting the oral cavity with any of the oral care compositions.

Also provided is a use, in an oral care composition, of a combination of (a) serine and (b) one or more zinc salts; to reduce or inhibit biofilm formation in an oral cavity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The present inventors have surprisingly found that the addition of serine to an oral care composition comprising a zinc salt improves the biofilm reduction efficacy of the oral care composition. The present inventors have also unexpectedly discovered that there is an optimal concentration of serine at which the biofilm reduction efficacy of the zinc salt-containing oral care composition is optimized.

In a first aspect, provided is an oral care composition comprising: (a) serine; and (b) zinc oxide and zinc citrate in a weight ratio of zinc oxide to zinc citrate of at least 1.5:1 to 4.5:1.

Optionally, the composition has a weight ratio of zinc oxide to zinc citrate of 1.5:1 to 4:1, 1.7:1 to 2.3:1, 1.9:1 to 2.1:1, or about 2:1. Also, the corresponding molar ratios based on these weight ratios can be used.

In a second aspect, provided is an oral care composition comprising: (a) serine and (b) at least one zinc salt; for use in reducing or inhibiting biofilm formation in an oral cavity. In some embodiments, the serine may be present in this composition in an amount of from 0.05 weight % to 0.8 weight %, from 0.05 weight % to 0.15 w eight %, or from 0.05 weight % to 0.39 weight %, based on the total weight of the composition.

In a third aspect, provided is a method of reducing or inhibiting biofilm formation in an oral cavity, the method comprising contacting the oral cavity with an oral care composition comprising (a) serine and (b) at least one zinc salt. In some embodiments, the serine may be present in this composition in an amount of from 0.05 weight % to 0.8 weight from 0.05 weight % to 0.75 weight %, or from 0.05 weight % to 0.39 weight %, based on the total weight of the composition.

In a fourth aspect, provided is for use, in an oral care composition, of a combination of (a) serine and (b) at least one zinc salt; to reduce or inhibit biofilm formation in an oral cavity. In some embodiments, the serine may be present in the oral care composition in an amount of from 0.05 weight % to 0.8 weight %, from 0.05 weight % to 0.75 weight %, or from 0.05 weight % to 0.39 weight %, based on the total weight of the composition.

In a fifth aspect, provided is an oral care composition in accordance with the first aspect, for use in reducing or inhibiting biofilm formation in an oral cavity.

In a sixth aspect, provided is a method of reducing or inhibiting biofilm formation in an oral cavity, the method comprising contacting the oral cavity with an oral care composition in accordance with the first aspect.

In each of the above aspects, serine may be present in the oral care composition in an amount of from 0.075 weight % to 0.35 weight %; from 0.075 weight % to 0.30 weight %; from 0.075 weight % to 0.25 weight %; from 0.12 weight % to 0.25 weight %; from 0.14 weight % to 0.20 weight %; from 0.14 weight % to 0.18 weight %; from 0.14 weight % to 0.16 weight %; or about 0.15 weight %, based on the total weight of the composition.

In any embodiments of each of the above aspects, the molar ratio of serine:total zinc salts may be from 0.01:1 to 3:1; from 0.01:1 to 2,2:1; from 0.02:1 to 1.4:1; from 0.05:1 to 0.3:1; from 0.1:1 to 0.2:1; or about 0.1:1.

Examples of suitable zinc salts which may be used in compositions of any of the above aspects include (but are not limited to): zinc oxide, zinc citrate, zinc lactate, zinc chloride, zinc acetate, zinc gluconate, zinc glycinate, zinc sulphate, sodium zinc citrate, and mixtures thereof. In any of the above aspects, at least one of the one or more zinc salts may be zinc oxide, Additionally or alternatively, at least one or the one or more zinc salts may be zinc citrate. In some embodiments, the total concentration of zinc salts in the composition is from 0.2 weight % to 5 weight %; from 0.5 weight % to 2.5 weight %; from 0.8 weight % to 2 weight %; or about 1.5 weight %, based on the total weight of the composition.

In any embodiments of each of the above aspects, the composition may comprise zinc oxide in an amount of from 0.5 weight % to 1.5 weight % and zinc citrate in an amount of from 0.25 weight % to 0.75 weight %, based on the total weight of the composition. Alternatively, the compositions may comprise zinc oxide in an amount of 0.75 weight % to 1.25 weight % and zinc citrate in an amount of 0.4 weight % to 0.6 weight %, based on the total weight of the composition. Alternatively, the compositions may comprise zinc oxide in an amount of about 1 weight % and zinc citrate in an amount of about 0.5 weight %, based on the total weight of the composition.

In any embodiments of each of the above aspects, the compositions may further comprise one or more abrasives. Suitable abrasives which may be included in the compositions include, but are not limited to: silica abrasives, aluminum oxide, aluminum silicate, calcined alumina, bentonite, other siliceous materials, insoluble phosphates, natural calcium carbonate, precipitated calcium carbonate, and mixtures thereof In some embodiments, at least one of the one or more abrasives is a silica abrasive. Examples of silica abrasives include, but are not limited to, precipitated or hydrated silicas having a mean particle size of up to about 20 microns (such as Zeodent 105 and Zeodent 114 marketed by J. M. Hither Chemicals Division, Havre de Grace, Md. 21078); Sylodent 783 (marketed by Davison Chemical Division of W. R. Grace & Company); or Sorbosil AC 43 (from PQ Corporation). In some embodiments, at least one of the one or more abrasives is a calcium carbonate abrasive, such as precipitated calcium carbonate (PCC) or natural calcium carbonate (NCC).

In any embodiments of each of the above aspects, the compositions may further comprise anticalculus tartar control) agent. Suitable anticalculus agents include, but are not limited to: phosphates and polyphosphates, polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, tetrasodium pyrophosphate (TSPP), tetrapotassium pyrophosphate, sodium tripolyphosphate, tetrapolyphosphate, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®. In some embodiments, the anticalculus agent is at least one of tetrasodium pyrophosphate and tetrapotassium pyrophosphate. In some embodiments, the anticalculus agent is present in the composition in an amount of from 0.2 weight % to 0.8 weight %; 0.3 weight % to 0.7 weight %; 0.4 weight % to 0.6 weight %; or about 0.5 weight %, based on the total weight of the composition.

In any embodiments of each of the above aspects, the oral care composition may be a dentifrice, a toothpaste, a gel, a tooth powder, a mouthwash, a mouthrinse, a lozenge, a tablet, a spray, a gum, or a film. In certain embodiments, the oral care composition is a toothpaste, a gel, or a tooth powder.

The oral care compositions may further comprise additional ingredients. These additional ingredients may include, but are not limited to, diluents, bicarbonate salts, pH modifying agents, surfactants, foam modulators, thickening agents, humectants, sweeteners, flavorants, pigments, additional antibacterial agents, anticaries agents, and mixtures thereof.

In some embodiments, the oral care compositions comprise at least one bicarbonate salt useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. The one or more additional bicarbonate salts are optionally present in a total amount of about 0.1 wt. % to about 50 wt. %, for example about 1 wt. % to 20 wt. %, by total weight of the composition.

In some embodiments, the oral care compositions comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, &odium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate), imidazole and the like. One or more pH modifying agents are optionally present in a total amount effective to maintain the composition in an orally acceptable pH range.

The oral care compositions may also comprise at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. Betaines may also be used, a suitable example of which is cocoamidopropyl betaine. One or more surfactants are optionally present in a total amount of about 0,01 wt. % to about 10 wt. %, for example, from about 0.05 wt. % to about 5 wt. %, or from about 0.1 wt. % to about 2 wt. % by total weight of the composition.

The oral care compositions may comprise at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt. % to about 10 wt. %, for example from about 0.2 wt. % to about 5 wt. %, or from about 0.25 wt. % to about 2 wt. %, by total weight of the composition.

The oral care compositions may comprise at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. Silica thickeners such as DT 267 (from PPG Industries) may also be used. One or more thickening agents are optionally present in a total amount of from about 0.01 wt. % to 15 wt. %, for example from about 0.1 wt. % to about 10 wt. %, or from about 0.2 wt. % to about 5 wt. %, by total weight of the composition.

The compositions may comprise at least one viscosity modifier, useful for example to help inhibit settling or separation of ingredients or to promote re-dispersibility upon agitation of a liquid composition. Any orally acceptable viscosity modifier can be used, including without limitation, mineral oil, petrolatum, clays and organomodified clays, silicas and the like. One or more viscosity modifiers are optionally present in a total amount of from about 0.01 wt. % to about 10 wt. %, for example, from about 0.1 wt. % to about 5 wt. %, by total weight of the composition.

The compositions may also comprise at least one humectant. Any orally acceptable humectant can be used, including without limitation, polyhydric alcohols such as glycerin, sorbitol (optionally as a 70 wt. % solution in water), xylitol or low molecular weight polyethylene glycols (PEGs). Most humectants also function as sweeteners. One or more humectants are optionally present in a total amount of from about 1 wt. % to about 70 wt. %, for example, from about 1 wt. % to about 50 wt. %, from about 2 wt. % to about 25 wt. %, or from about 5 wt. % to about 15 wt. %, by total weight of the composition.

The oral care compositions may comprise at least one sweetener, useful for example to enhance taste of the composition. One or more sweeteners are optionally present in a total amount depending strongly on the particular sweetener(s) selected, but typically 0.005 wt. % to 5 wt. %, by total weight of the composition, optionally 0.005 wt. % to 0.2 wt. %, further optionally 0.05 wt. % to 0.1 wt. % by total weight of the composition.

The compositions may also comprise at least one flavorant, useful for example to enhance taste of the composition. Any orally acceptable natural or synthetic flavorant can be used, including without limitation tea flavours, vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropyibutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt. % to about 5 wt. %, for example, from about 0.03 wt. % to about 2.5 wt. %, optionally about 0.05 wt. % to about 1.5 wt. %, further optionally about 0.1 wt. % to about 0.3 wt. % by total weight of the composition.

The compositions may comprise at least one colorant. Colorants herein include pigments, dyes, lakes and agents imparting a particular luster or reflectivity such as pearling agents. Any orally acceptable colorant can be used, including without limitation talc, mica, magnesium carbonate, magnesium silicate, magnesium aluminum silicate, titanium dioxide, red, yellow, brown and black iron oxides, ferric ammonium ferrocyanide, manganese violet, ultramarine, titaniated mica, bismuth oxychloride, and the like. One or more colorants are optionally present in a total amount of from about 0.001 wt. % to about 20 wt. %, for example, from about 0.01 wt. % to about 10 wt. %, or from about 0.1 wt. % to about 5 wt. %, by total weight of the composition.

The compositions may also comprise an additional antibacterial or preservative agent, such as chlorhexidine, triclosan, quaternary ammonium compounds (for example benzalkonium chloride) or parabens such as methylparaben or propylparaben. One or more additional antibacterial or preservative agents may optionally be present in the composition in a total amount of from about 0.01 wt. % to about 0.5 wt. %, optionally about 0.05 wt. % to about 0.1 wt. % by total weight of the composition.

The oral care compositions may also comprise a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluomsilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monafluorophosphate, as well as mixtures thereof. In certain embodiments, the oral care composition may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The compositions may comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions may include antisensitivity agents, e.g., potassium salts such as potassium nitrate, potassium bicarbonate, potassium chloride, potassium citrate, and potassium oxalate; capsaicin; eugenol; strontium salts; chloride salts and combinations thereof. Such agents may be added in effective amounts, e.g., from about 1 wt. % to about 20 wt. % by weight based on the total weight of the composition, depending on the agent chosen.

The composition may further comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

EXAMPLES

Experiments were carried out in order to evaluate the biofilm reduction efficacy of compositions containing different concentrations of serine. Formulations containing either silica or natural calcium carbonate (NCC) as an abrasive were tested.

In all of the Examples, below, the experimental methodology used was the Biofilm Growth Inhibition University of Manchester Model. The protocol for this model is as follows:

(1) Dental plaque was collected from four healthy volunteers and pooled together as inoculum. The Optical Density of the inoculum was matched to 0.3 absorbance at 610 nm (2) Sterile hydroxyapatite (HAP) disks were incubated under anaerobic conditions at 37° C. for 24 hours with 1 mL of sterile artificial saliva (with 0.01 weight % sucrose) and 1 mL of pooled saliva in a 24 well microplate.

(3) For each test dentifrice (and for each control) a treatment solution of 1 part dentifrice: 2 parts sterile distilled water by weight was made up. Each freshly prepared treatment solution was added to three wells and allowed to contact the HAP disk therein for 10 minutes.

(4) The liquid phase of each well was then removed and was replaced by 2 mL sterile artificial saliva.

(5) The disks were then maintained at 37° C. under anaerobic conditions for 8 days.

(6) At intervals of 2, 4 and 8 days, the disks were collected aseptically and transferred to half-strength pre-reduced thioglycollate medium (4.5 ml per disk).

(7) 100 µL of the dilution 10-4, 10-5 and 10-6 were plated in duplicates for each disk on Neomycin/Vancomycin (NV) Agar for Total Gram-negative Anaerobes.

(8) The plates were surface-spread using a sterile spreader and were incubated anaerobically at 37° C. for 72 hours, after which time the number of colonies on each plate was counted.

The log 10 CFU/ml (where CFU=colony forming units) for each test dentifrice or control was calculated. A lower Log 10 CFU/ml indicates that the dentifrice tested has greater efficacy in inhibiting biofilm growth.

The results of the tests are shown in Examples 1 to 3, below.

Example 1

In the first round of biofilm reduction tests, the formulations as listed in Table 1 were evaluated for their ability to reduce biofilm growth. The results obtained using the Biofilm Growth Inhibition University of Manchester Model methodology (above) are shown in Table 1, with the average log 10 CFU/ml obtained from the disk incubated for 8 days in step 6 of the method.

TABLE 1

| No. | Formula | Avg. log10 CFU/ml |
| --- | --- | --- |
| 1 | Silica (no Zn or serine) | 6.38 |
| 2 | Silica, 1 weight % ZnO, 0.5 weight % ZnCit, 0.5 weight % TSPP, no serine | 5.54 |
| 3 | NCC, 1 weight % ZnO, 0.5 weight % ZnCit, 0.5 weight % TSPP, no serine | 5.29 |
| 4 | NCC, 1 weight % ZnO, 0.5 weight % ZnCit, 0.5 weight % TSPP, 0.75 weight % serine | 4.88 |
| 5 | NCC, 1 weight % ZnO, 0.5 weight % ZnCit, 0.5 weight % TSPP, 0.25 weight % serine | 4.78 |
| 6 | Silica, 1 wt % ZnO, 0.5 weight % ZnCit, 0.5 weight % TSPP, 0.75 weight % serine | 4.76 |
| 7 | Silica, 1 wt % ZnO, 0.5 weight % ZnCit, 0.5 weight % TSPP, 0.25 weight % serine | 4.71 |

The results as shown in Table 1 showed that formulae containing serine have improved efficacy in biofilm reduction, independent of the type of abrasive used (silica or natural calcium carbonate). There was also no significant difference in efficacy between formulae containing 0.25 weight % serine and 0.75 weight % serine.

Example 2

To investigate whether there was an optimum concentration of serine at which the efficacy of biofilm reduction is maximized, a second round of biofilm reduction tests was carried out using the formulations listed in Table 2, below, in a dentifrice. All of the test dentifrices contain 1 weight % ZnO and 0.5 weight % Zn citrate. In the results below, formulae sharing the same letter for "statistical significance" do not show a significant difference in their biofilm reduction efficacy.

TABLE 2

| No. | Formula | Avg. log10 CFU/ml |
| --- | --- | --- |
| 1 | NCC, 1 weight % ZnO, 0.5 weight % ZnCit, no serine | 6.5 |
| 2 | Silica, 1 weight % ZnO, 0.5 weight % ZnCit, no serine | 6.4 |
| 3 | NCC, 1 weight % ZnO, 0.5 weight % ZnCit, 0.075 weight % serine | 6.2 |
| 4 | Silica, 1 weight % ZnO, 0.5 weight % ZnCit, 0.075 weight % serine | 6.1 |
| 5 | Silica, 1 weight % ZnO, 0.5 weight % ZnCit, 0.25 weight % serine | 5.8 |
| 6 | NCC, 1 weight % ZnO, 0.5 weight % ZnCit, 0.25 weight % serine | 5.8 |
| 7 | NCC, 1 weight % ZnO, 0.5 weight % ZnCit, 0.15 weight % serine | 5.7 |
| 8 | Silica, 1 weight % ZnO, 0.5 weight % ZnCit, 0.15 weight % serine | 5.5 |

As can be seen from Table 2, above, 0.15 weight % serine in the silica-containing formulation outperformed all the other formulae tested, as indicated by a significantly lower value of average Log10 CFU/ml. This was followed by 0.15 weight % serine in the NCC-containing formula, then by 0.25 weight % serine in the silica or NCC containing formulae, and then by 0.075 weight % serine in the silica or NCC-containing formulae. As in Example 1, the formulations containing serine showed improved efficacy in biofilm reduction as compared to formulations without serine. The results obtained in this example also indicate that the biofilm reduction efficacy of the formulations was independent of whether they contained silica or NCC as the abrasive.

Example 3

The tests of Example 2 were then repeated. In the results below, formulae sharing the same letter for "statistical significance" do not show a significant difference in their biofilm reduction efficacy.

TABLE 3

| No. | Formula | Avg. log10 CFU/ml | Statistical significance |
| --- | --- | --- | --- |
| 1 | NCC, 1 weight % ZnO, 0.5 weight % ZnCit, no serine | 6.34 | A |
| 2 | Silica, 1 weight % ZnO, 0.5 weight % ZnCit, no serine | 6.24 | AB |
| 3 | NCC, 1 weight % ZnO, 0.5 weight % ZnCit, 0.075 weight % serine | 6.04 | AB |
| 4 | Silica, 1 weight % ZnO, 0.5 weight % ZnCit, 0.075 weight % serine | 6.00 | B |
| 5 | Silica, 1 weight % ZnO, 0.5 weight % ZnCit, 0.25 weight % serine | 5.6 | C |
| 6 | NCC, 1 weight % ZnO, 0.5 weight % ZnCit, 0.25 weight % serine | 5.5 | CD |
| 7 | NCC, 1 weight % ZnO, 0.5 weight % ZnCit, 0.15 weight % serine | 5.27 | DE |
| 8 | Silica, 1 weight % ZnO, 0.5 weight % ZnCit, 0.15 weight % serine | 5.03 | E |

As shown above, the results obtained in Example 3 were similar to those obtained in Example 2. From the results of Examples 2 and 3, it can be seen that the biofilm reduction performance of the test samples increases as the concentration of serine increases from 0 weight % to 0.15 weight %, and that the performance declines at higher serine concentrations (e.g. 0.25 weight %), but the performance is still better than zinc alone, Formulations containing 0.15 weight % serine performed better in terms of their biofilm. reduction efficacy than those formulations containing higher or lower concentrations of serine, for both silica-based and NCC-based formulations.

What is claimed is:
1. An oral care composition comprising:
a. serine; and
b. zinc oxide and zinc citrate in a weight ratio of zinc oxide to zinc citrate of 2:1,
wherein serine is present in the composition in an amount of 0.14 weight % to 0.2 weight % based on the total weight of the composition; and
wherein the composition comprises zinc oxide in an amount of 0.5 weight % to 1.5 weight % and zinc citrate in an amount of from 0.25 weight % to 0.75 weight %, based on the total weight of the composition.
2. The oral care composition of claim 1, wherein the composition comprises serine in an amount of about 0.15 weight %, based on the total weight of the composition.
3. The oral care composition of claim 1, wherein the total concentration of zinc oxide and zinc citrate in the composition is 0.2 weight % to 5 weight %, based on the total weight of the composition.
4. The oral care composition of claim 1, wherein the composition comprises zinc oxide in an amount of about 1 weight % and zinc citrate in an amount of about 0.5 weight %, based on the total weight of the composition.

5. An oral care composition comprising:
a. serine and
b. one or more zinc salts,
for use in reducing or inhibiting biofilm formation in an oral cavity,
wherein serine is present in the composition in an amount of 0.14 weight % to 0.20weight % based on the total weight of the composition;
and wherein the one or more zinc salts comprise zinc oxide in an amount of from 0.5weight % to 1.5 weight % and zinc citrate in an amount of from 0.25 weight % to 0.75weight %, based on the total weight of the composition; and
wherein a weight ratio of zinc oxide to zinc citrate is 2:1.

6. The oral care composition of claim 5, wherein the composition comprises serine in an amount of about 0.15 weight %, based on the total weight of the composition.

7. The oral care composition of claim 5, wherein the molar ratio of serine:total zinc salts is from 0.01:1 to 3:1.

8. The oral care composition of claim 5, wherein the total concentration of zinc salts in the composition is from 0.2 weight % to 5 weight %, based on the total weight of the composition.

9. The oral care composition of claim 5, wherein the composition comprises zinc oxide in an amount of about 1 weight % and zinc citrate in an amount of about 0.5 weight %, based on the total weight of the composition.

10. A method of reducing or inhibiting biofilm formation in an oral cavity, the method comprising contacting the oral cavity with an oral care composition of claim 1.

11. The oral care composition of claim 1, wherein the composition further comprises stannous fluoride.

12. The oral care composition of claim 5, wherein the composition further comprises stannous fluoride.

* * * * *

UNITED STATES PATENT AND TRADEMARK OFFICE
CERTIFICATE OF CORRECTION

PATENT NO. : 10,576,032 B2
APPLICATION NO. : 15/104780
DATED : March 3, 2020
INVENTOR(S) : Michael Prencipe et al.

Page 1 of 1

It is certified that error appears in the above-identified patent and that said Letters Patent is hereby corrected as shown below:

In the Specification

In Column 3, Line 16, delete "0.15 w eight%," and insert -- 0.75 weight%, --, therefor.

In Column 4, Line 26, delete "Hither" and insert -- Huber --, therefor.

In Column 4, Line 34, after "further comprise", insert -- an --.

In Column 5, Line 25, delete "&odium" and insert -- disodium --, therefor.

In Column 5, Line 53, delete "0,01" and insert -- 0.01 --, therefor.

In Column 7, Lines 8-9, delete "N,2,3-trimethyl-2-isopropyibutanamide," and insert -- N,2,3-trimethyl-2-isopropylbutanamide, --, therefor.

In Column 7, Lines 43-44, delete "fluomsilicate," and insert -- fluorosilicate, --, therefor.

In Column 7, Line 49, delete "monafluorophosphate," and insert -- monofluorophosphate, --, therefor.

In the Claims

In Column 11, Line 9, in Claim 5, delete "0.20weight" and insert -- 0.20 weight --, therefor.

In Column 11, Line 12, in Claim 5, delete "0.5weight" and insert -- 0.5 weight --, therefor.

In Column 11, Line 14, in Claim 5, delete "0.75weight" and insert -- 0.75 weight --, therefor.

Signed and Sealed this
Second Day of June, 2020

Andrei Iancu
*Director of the United States Patent and Trademark Office*